United States Patent
Missling

(10) Patent No.: US 11,446,275 B2
(45) Date of Patent: *Sep. 20, 2022

(54) NEURODEVELOPMENTAL DISORDER THERAPY

(71) Applicant: ANAVEX LIFE SCIENCES CORP., New York, NY (US)

(72) Inventor: Christopher U. Missling, New York, NY (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/145,073

(22) Filed: Jan. 8, 2021

(65) Prior Publication Data

US 2021/0228532 A1 Jul. 29, 2021

Related U.S. Application Data

(63) Continuation of application No. 16/717,921, filed on Dec. 17, 2019, now Pat. No. 10,888,543, which is a continuation of application No. 16/068,703, filed as application No. PCT/US2017/014702 on Jan. 24, 2017, now Pat. No. 10,507,196.

(60) Provisional application No. 62/287,062, filed on Jan. 26, 2016.

(51) Int. Cl.
*A61K 31/341* (2006.01)
*A61P 25/00* (2006.01)

(52) U.S. Cl.
CPC ............ *A61K 31/341* (2013.01); *A61P 25/00* (2018.01)

(58) Field of Classification Search
CPC .............................. A61K 31/341; A61P 25/00
USPC ......................................................... 514/471
See application file for complete search history.

(56) References Cited

U.S. PATENT DOCUMENTS 10,507,196 B2 12/2019 Missling
10,888,543 B2 1/2021 Missling

FOREIGN PATENT DOCUMENTS

| EA | 201390616 A1 | 9/2013 |
|---|---|---|
| EP | 2850190 B1 | 7/2020 |
| GR | 1004208 B | 4/2003 |
| GR | 1006794 B | 6/2010 |
| WO | 1997030983 A1 | 8/1997 |
| WO | 2008153929 A1 | 12/2008 |

OTHER PUBLICATIONS

International Search Report and Written Opinion dated Apr. 4, 2017 in corresponding International Application No. PCT/US2017/014702, 13 pages.
International Preliminary Report on Patentability dated Jul. 31, 2-18 in corresponding International Application No. PCT/US2017/014702, 9 pages.
European Communication pursuant to Article 94(3) EPC dated Apr. 17, 2020 in corresponding European Patent Application No. 17703579.7, 4 pages.
Anavex Life Sciences: "Assessment of Anavex 2-73 in a MECP2 Re5 Syndrome Mouse Model 2016 Epilepsy Pipeline Conference Feb. 26, 2016", retrieved from the internet URL: http://anavex.com/wp-content/uploads/assessment-of-anavex-2-73-in-a-MECP2-Rett-Syndrome-Mouse-Model.pdf, 19 pages.
Hagebeuk, "UVA-DARE (Digital Academic Repository)," Rett Syndrome: Neurologic and Metabolic Aspects—PhD thesis, Nov. 7, 2013, 24 pages.
Lyst, et al., "Rett Syndrome: a complex disorder with simple roots," Nature Reviews Genetics, vol. 16, No. 5, Mar. 3, 2015, 13 pages.
Rebowe, et al., "Anavex 2-73 as a Potential Treatment for Rett Syndrome and Other Pediatric or Infantile Disorders with Seizure Pathology," 2016 Rett Syndrome Symposium Jun. 22-24, 2016, Retrieved from the Internet: http://anavex.com/wp-content/uploads/ANAVEX-2-73-as-Potential-Treatment-for-Rett-Syndrome.pdf, 30 pages.

*Primary Examiner* — Kristin A Vajda
(74) *Attorney, Agent, or Firm* — Polsinelli PC

(57) ABSTRACT

This invention addresses tetrahydro-N, N-dimethyl-2,2diphenyl-3-furanmethanamine hydrochloride (ANAVEX2-73, AV2-73, or A2-73) in a method of treatment for neurodevelopmental disorders. Particular reference is made to the treatment of autism spectrum disorder, cerebral palsy, Rett syndrome, Angelman syndrome, Williams syndrome, pervasive developmental disorder not otherwise specified (PDD-NOS), childhood disintegrative disorder, and Smith-Magenis syndrome. Additional reference is made to multiple sclerosis.

20 Claims, 11 Drawing Sheets

FIG. 4A
FIG. 4B
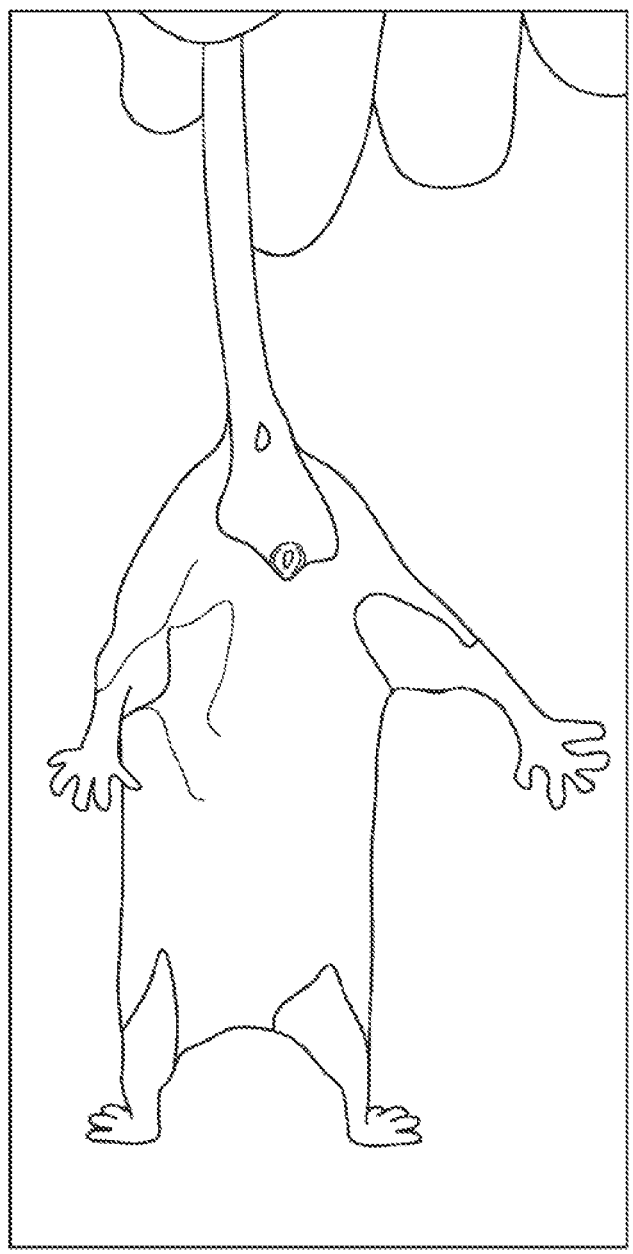
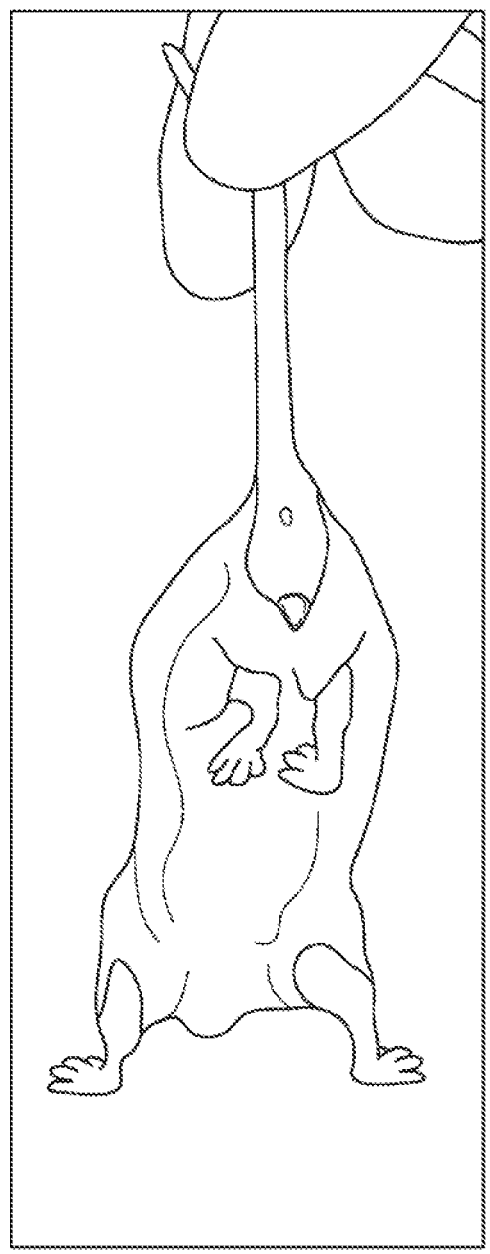

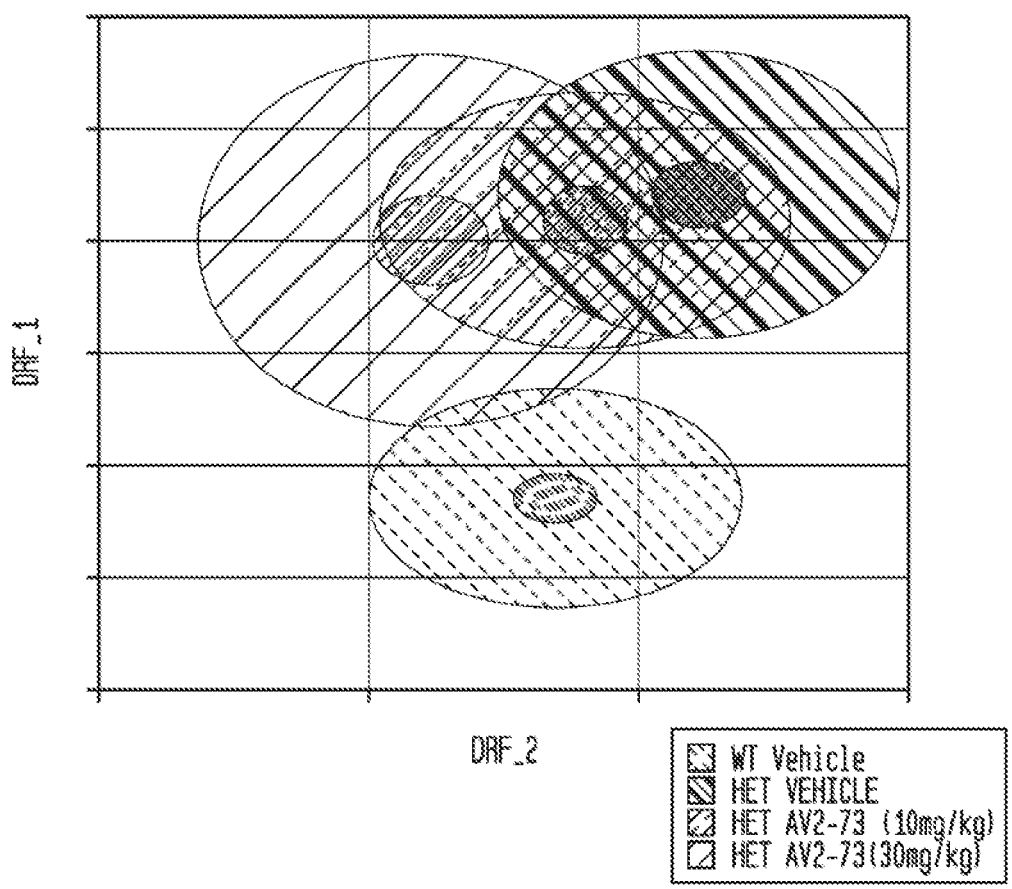

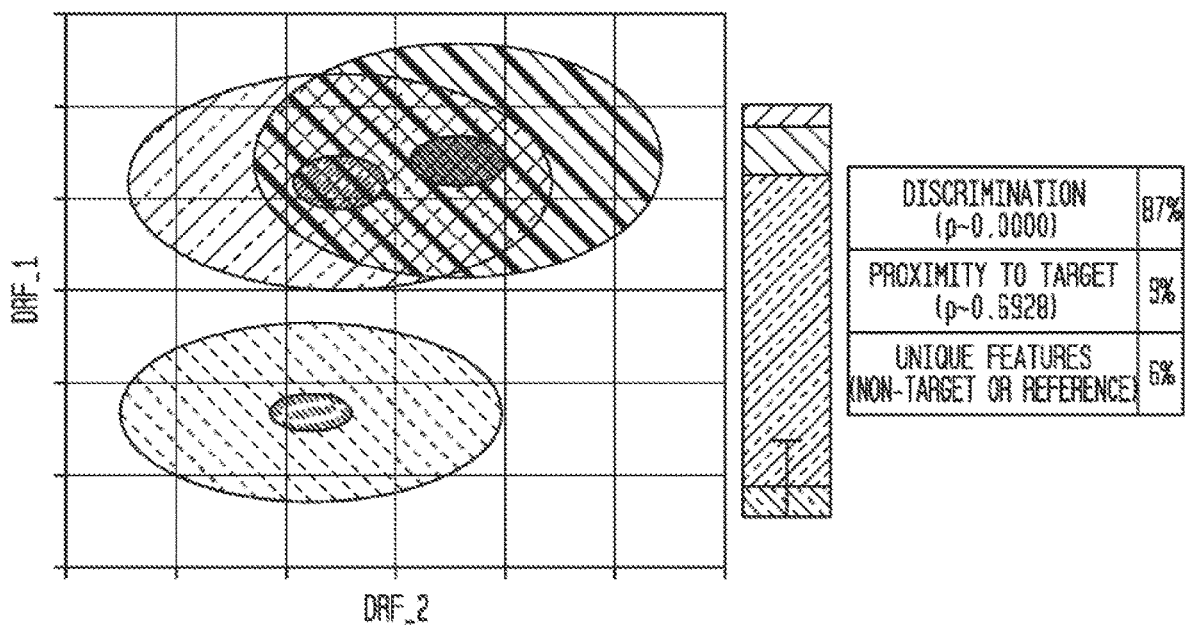
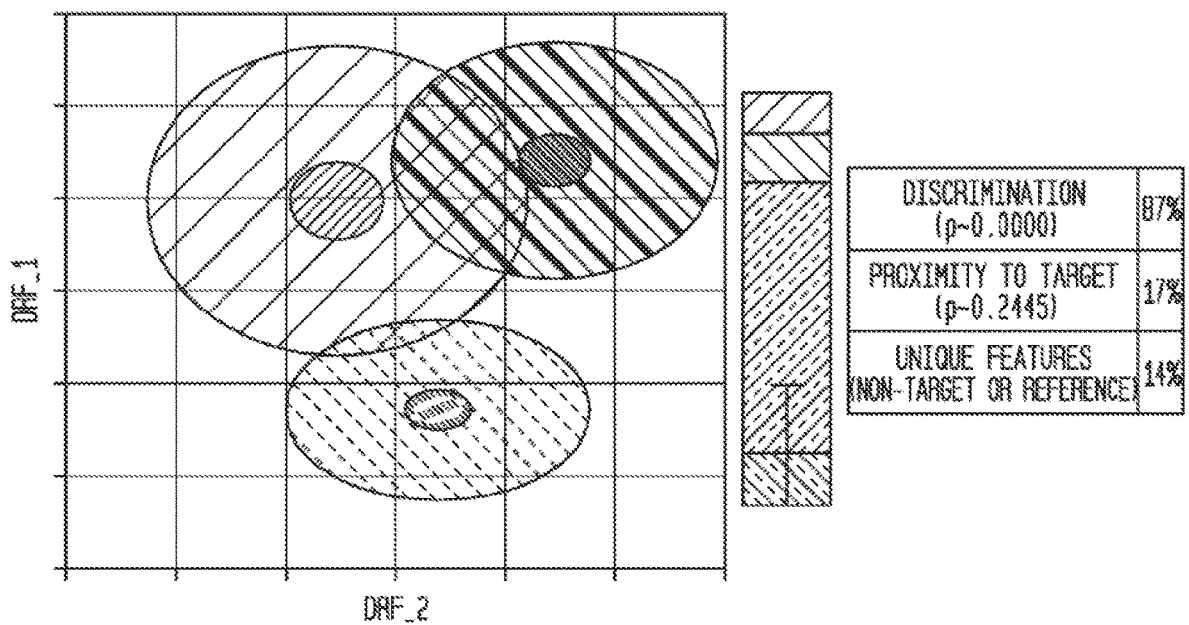

NEURODEVELOPMENTAL DISORDER THERAPY

CROSS-REFERENCE TO RELATED APPLICATIONS

This application is a continuation of U.S. patent application Ser. No. 16/717,921 filed Dec. 17, 2019, which is a continuation of U.S. patent application Ser. No. 16/068,703 filed Jan. 15, 2019, which is a national stage filing under 35 U.S.C. § 371 of International Application No. PCT/US2017/014702, filed Jan. 24, 2017, which claims the benefit of U.S. Provisional Application No. 62/287,062 filed Jan. 26, 2016, the disclosure of each of which is hereby incorporated by reference in its entirety.

FIELD OF THE INVENTION

This invention addresses tetrahydro-N, N-dimethyl-2,2-diphenyl-3-furanmethanamine hydrochloride (ANAVEX™ 2-73, AV2-73, or A2-73) in a method of treatment for neurodevelopmental disorders. Particular reference is made to the treatment of autism spectrum disorder, cerebral palsy, Rett syndrome, Angelman syndrome, Williams syndrome, pervasive developmental disorder not otherwise specified (PDD-NOS), childhood disintegrative disorder, and Smith-Magenis syndrome. Additional reference is made to multiple sclerosis therapy.

BACKGROUND OF THE INVENTION

Neurodevelopmental disorders are generally categorized as disorders associated with changes in early brain development. These typically exhibit themselves as behavioral and cognitive alterations in sensory and motor systems, speech, and language. Particular reference is made to autism spectrum disorder, cerebral palsy, Rett syndrome, Angelman syndrome, Williams syndrome, and Smith-Magenis syndrome.

Rett syndrome (RTT), originally termed cerebroatrophic hyperammonemia, is a rare genetic postnatal neurological disorder of the grey matter of the brain that almost exclusively affects females but has also been found in male patients. The clinical features include small hands and feet and a deceleration of the rate of head growth (including microcephaly in some). Repetitive stereotyped hand movements, such as wringing and/or repeatedly putting hands into the mouth, are also noted. People with Rett syndrome are prone to gastrointestinal disorders and up to 80% have seizures. They typically have no verbal skills, and about 50% of affected individuals do not walk. Scoliosis, growth failure, and constipation are very common and can be problematic.

The signs of this disorder are most easily confused with those of Angelman syndrome, cerebral palsy, and autism. Rett syndrome occurs in approximately 1:10,000 live female births in all geographies, and across all races and ethnicities.

Without being bound by any particular theory it is believed that Rett syndrome is caused by mutations in the gene MECP2 located on the X chromosome (which is involved in transcriptional silencing and epigenetic regulation of methylated DNA), and can arise sporadically or from germline mutations. Reportedly, in less than 10% of RTT cases, mutations in the genes CDKL5 or FOXG1 have also been found to resemble it. Rett syndrome is initially diagnosed by clinical observation, but the diagnosis is definitive when there is a genetic defect in the MECP2 gene.

Tetrahydro-N,N-dimethyl-2,2-diphenyl-3-furanmethanamine hydrochloride (ANAVEX2-73, AV2-73, or A2-73) is a compound which is believed to bind to muscarinic acetylcholine and sigma-1 receptors with affinities in the low micromolar range. It has been reported that A2-73 showed neuroprotective potential against amyloid toxicity in mice. In particular, A2-73 has been reported as attenuating oxidative stress, caspases induction, cellular loss and learning and memory deficits observed in mice one week after the i.v. injection of an oligomeric preparation of amyloid β25-35 peptide (Aβ25-35) (Villard et al., *J. Psychopharmacol.* 2011). More recently, it has been reported that A2-73 blocked the Aβ25-35-induced P-Akt decrease and P-GSK-3β increase, indicating activation of the PI3K neuroprotective pathway (Lahmy et al., *Neuropsychopharmacology,* 2013). In the dose-range tested, A2-73 attenuated the hyperphosphorylation of Tau on physiological epitopes (AT-8 antibody clone) and on pathological epitopes (AT-100 clone). A2-73 also has been reported decreasing the Aβ25-35-induced endogenous Aβ1-42 seeding.

It has been reported that neurodevelopmental disorders respond to N-methyl-D-aspartate receptor (NMDAR) antagonists and combination therapy. Reference is made to NMDAR antagonists selected from the group consisting of Amantadine, AZD6765, Dextrallorphan, Dextromethorphan, Dextrorphan, Diphenidine, Dizocilpine (MK-801), Ethanol, Eticyclidine, Gacyclidine, Ibogaine, Memantine, Methoxetamine, Nitrous oxide, Phencyclidine, Rolicyclidine, Tenocyclidine, Methoxydine, Tiletamine, Xenon, Neramexane, Eliprodil, Etoxadrol, Dexoxadrol, WMS-2539, NEFA, Delucemine, 8A-PDHQ, Aptiganel, HU-211, Remacemide, Rhynchophylline, Ketamine, 1-Aminocyclopropanecarboxylic acid (ACPC), 7-Chlorokynurenate' DCKA (5,7-dichlorokynurenic acid), Kynurenic acid, Lacosamide, L-phenylalanine, Neurotransmitters, Psychedelics, Long-term potentiation, and NMDA.

Reference is made to the following publications. These publications, and all publications cited herein, are incorporated by reference in their entirety:

1. "Rett Syndrome Fact Sheet. NIH Publication No. 09-4863". National Institute of Neurological Disorders and Stroke (NINDS). November 2009.
2. Guy et al., (2007). "Reversal of Neurological Defects in a Mouse Model of Rett Syndrome." *Science* 315 (5815): 1143-7. doi:10.1126/science.1138389. PMID 17289941.
3. Trappe et al, "MECP2 Mutations in Sporadic Cases of Rett Syndrome Are Almost Exclusively of Paternal Origin." *The American Journal of Human Genetics* 68 (5): 1093-101.
4. Fitzgerald et al (1990). "Rett syndrome and associated movement disorders". *Movement Disorders* 5 (3): 195-202.
5. Ricceri et al (2008). "Mouse models of Rett syndrome: From behavioural phenotyping to preclinical evaluation of new therapeutic approaches". *Behavioural Pharmacology* 19 (5-6): 501-17. doi:10.1097/FBP.0b013e32830c3645. PMID 18690105.
6. Lombardi, et al, "MECP2 disorders: from the clinic to mice and back," *J Clin Invest.* 2015 Aug. 3; 125(8): 2914-23. doi: 10.1172/JCI78167. Epub 2015 Aug. 3. Review.
7. Pohodich et al, "Rett syndrome: disruption of epigenetic control of postnatal neurological functions." *Hum Mol Genet.* 2015 Oct. 15; 24 (R1): Epub 2015 Jun. 9.

8. Lotan et al, *Rett Syndrome: Therapeutic Interventions (Disability Studies)* 1st Ed (Nova Science Publishers, Inc 2011) PMID: 26060191.
9. U.S. Pat. No. 9,180,106 (Vamvakides) "Sigma receptors ligands with anti-apoptotic and/or pro-apoptotic properties, over cellular mechanisms, exhibiting prototypical cytoprotective and also anti-cancer activity."
10. Mallon et al, "EuroPhenome and EMPReSS: online mouse phenotyping resource," *Nucleic Acids Res.* 2008 January; 36 (Database issue): D715-8. Epub 2007 Sep. 28.
11. Morgan et al, "EuroPhenome: a repository for high-throughput mouse phenotyping data,". *Nucleic Acids Res.* 2010 January; 38 (Database issue): D577-85. doi: 10.1093/nar/gkp1007. Epub 2009 Nov. 23.
12. Tropea et al., "Partial reversal of Rett Syndrome-like symptoms in MeCP2 mutant mice". Proceedings of the National Academy of Sciences 106 (6): 2029-34. (2009),
13. Tan et al., "Pharmacological therapies for Angelman syndrome," *Wien Med Wochenschr.* 2016 Jan. 12. [Epub ahead of print]
14. US Pub. No 2015/0152410 to Kreig et al., entitled "Compositions And Methods For Modulating Mecp2 Expression."
15. US Pub. No 2015/0265554 to Roux et al, "Treatment of MeCP-2 Associated Disorders."
16. U.S. Pat. No. 7,994,127 to Sur et al., Treatment of Rett Syndrome And Other Disorders.

SUMMARY OF THE INVENTION

The claimed invention concerns a method of treating a neurodevelopmental disorders such as Rett syndrome in a subject by administering to said subject a therapeutically effective amount of A2-73. In particular embodiments this includes a dosage form comprising a therapeutic amount of A2-73. Note is made of the dosages of A2-73 from about 0.5 to about 500 mg. This invention further includes a therapeutic method of treating neurodevelopmental disorders such as autism spectrum disorder, cerebral palsy, Rett syndrome, Angelman syndrome, Williams syndrome, and Smith-Magenis syndrome. Additional mention is made of multiple sclerosis therapy using A2-73.

Therapeutic doses of A2-73 are particularly noted in a range of from about 0.5 mg/day to about 100 mg/day with particular reference to doses of from about 1 to about 60 mg/day and, optionally, wherein said dosage is administered daily for at least about 10 days. Adult doses of about 20 mg to about 50 mg/day are noted, with particular reference to about 30 mg to about 40 mg/day. Infant and child doses are to the lower end of the range with particular reference to from about 0.5 mg/day to about 20 mg/day. Chronic administration for chronic conditions is further contemplated. Further contemplate is the therapeutic use of A2-73 analogues tetrahydro-N,N-dimethyl-5,5-diphenyl-3-furanmethanamine hydrochloride (ANAVEX™ 1-41), and 1-(2,2-diphenyltetrahydrofuran-3-yl)-N-methylmethanamine hydrochloride (ANAVEX™ 19-144, or A19-144). These A2-73 analogues are contemplated for use at dosages and dosage ranges similar to A2-73.

BRIEF DESCRIPTION OF THE DRAWINGS

FIGS. 4A and 4B are pictures of mice showing unclasped and clasped hind leg responses.

FIGS. 8A-C show Neurocube data (8 week old mice).

DETAILED DESCRIPTION OF THE INVENTION

As used herein, "therapeutically effective amount" of an agent or combination of agents is an amount sufficient to achieve a desired therapeutic or pharmacological effect. Particular reference is made to an amount that is capable of ameliorating biochemical and functional abnormalities associated with loss-of-function mutations of the gene encoding methyl-CpG binding protein 2 (MeCP2). It is to be understood that a therapeutically effective amount of an agent or combinatory therapy may vary according to factors such as the disease state, age, and weight of the subject, and the ability of the agent to elicit a desired response in the subject. Dosage regimens may be adjusted to provide the optimum therapeutic response. A therapeutically effective amount is also one in which any toxic or detrimental effects of the active compound are outweighed by the therapeutically beneficial effects.

Studies employed wild type (WT) mice and heterozygous MECP2 knockout mice (HET) All mice were provided by Jackson Laboratory, Bar Harbor, Me. HET mice were Bird mice (Jackson Laboratories, Bar Harbor, Me., B6.129P2(C)-Mecp2$^{tm1.1Bird}$/Stock Number: 003890) were obtained by crossing het females with wild type (WT) males (C57B/6J). 129P2(C)-Mecp2$^{tm1.1Bird}$/J is a constitutive Mecp2 knockout that exhibits Rett syndrome-like neurological defects.

Breeding of the test mice done at Jackson Laboratories (Farmington Connecticut). Mice were shipped at 4-5 weeks of age.

Mecp2 females testing at ~8 and ~12 weeks of age
20 WT—vehicle (0.25% MC/dH2O)
20 HET—vehicle (0.25% MC/dH2O)
20 HET—A2-733 (10 mg/kg)
20 HET—A2-733 (30 mg/kg)

Chronic dosing (p.o.) daily, starting at ~5.5 weeks of age and continuing through the 12-week behavioral testing time point 60 min pre-treatment during behavioral testing.

Body Weight

Figure 1:
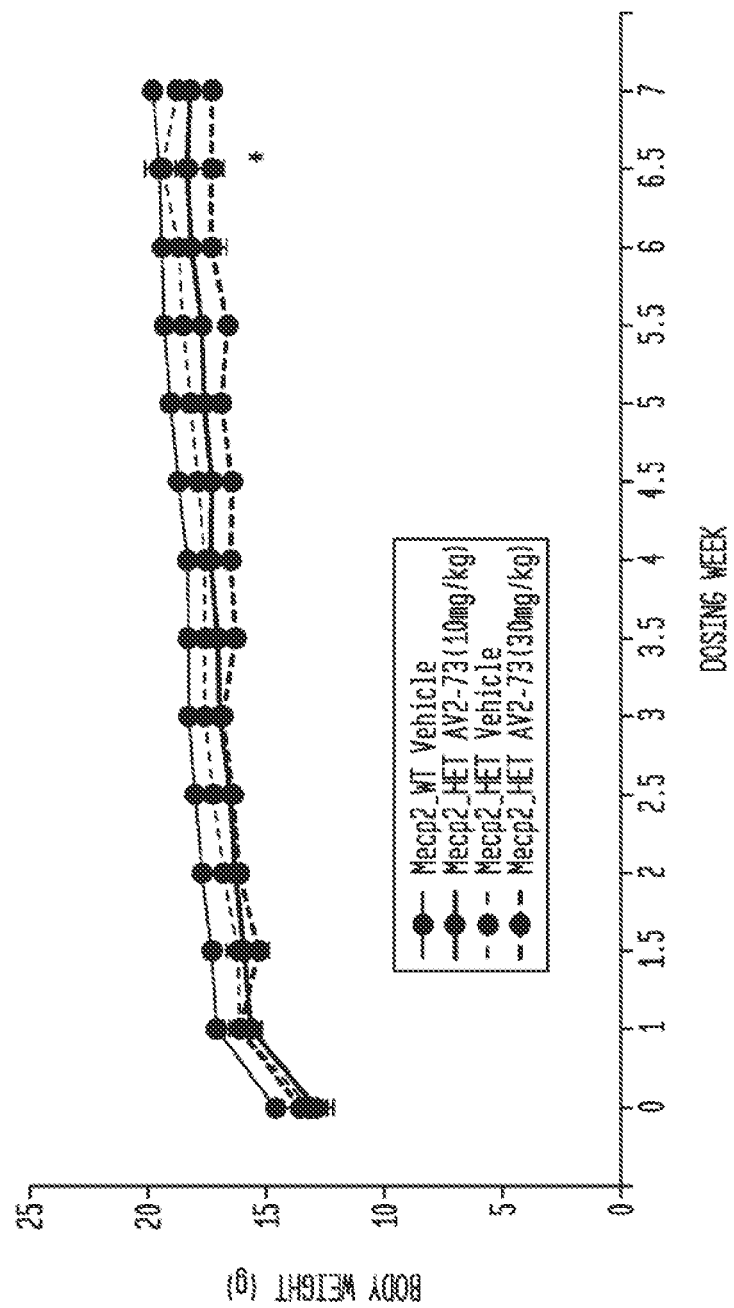
FIG. 1 is a graphic presentation of body weight of vehicle-treated and wild-type and mutant control mice.

No differences were observed in body weight between vehicle-treated wild-type and mutant control mice. FIG. 1 There was a significant Treatment×Age effect (p<0.001), where mice treated with A2-733 (30 mg/kg) weighed less than vehicle-treated mutant mice 6.5 weeks after dosing began.

Rotarod

The rotarod performance test is a performance test based on a rotating rod with forced motor activity being applied, usually by a rodent. The test measures parameters such as riding time (seconds) or endurance. Some of the functions of the test include evaluating balance, grip strength, and motor coordination of the subjects; especially in testing the effect of experimental drugs or after traumatic brain injury.

Mice are placed on the rotarod apparatus (PsychoGenics, Tarrytown N.Y.) consisting of a rod that rotates at a constant or variable and accelerating speed of 4 rpm. Once a mouse loses its balance and falls onto an underlying platform the timer automatically stops. Mice are exposed to the apparatus for 5 min training at a constant speed and placed back on the rod after each fall. After a rest period of at least 1 hr. animals are placed back on the rotarod apparatus for testing. Once all animals in a test session are loaded on the rod, the rotarod apparatus is placed on accelerating speed (0-40 rpm) over 5 min and the time until the first fall is recorded. The test is repeated three consecutive times per animal. For each test session, the RPM score at time of fall off the rod are recorded.

Figure 2A:
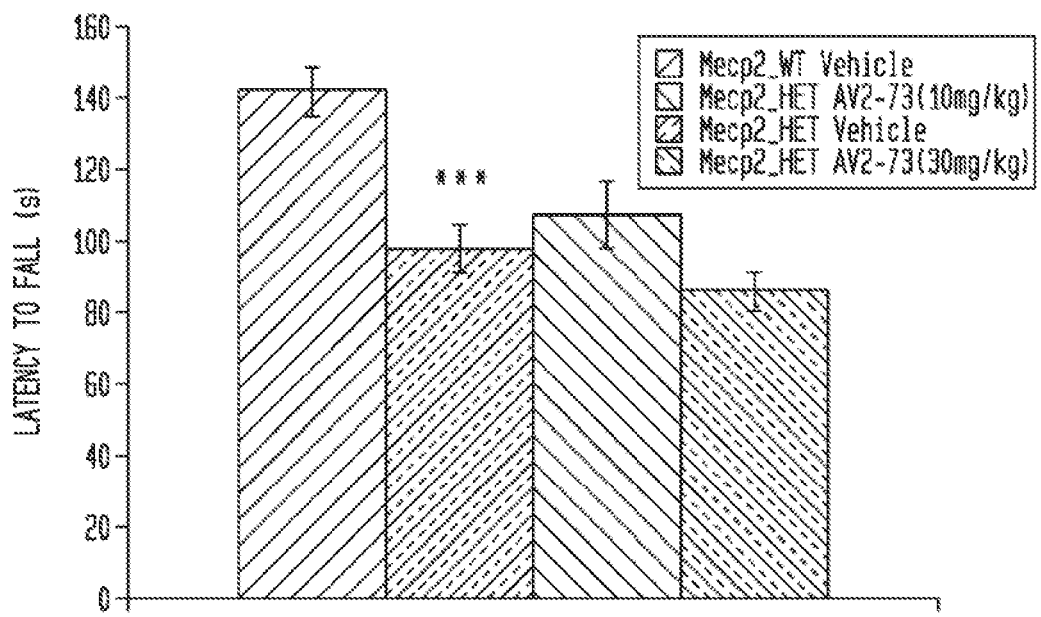
FIGS. 2A and 2B are graphic representations of rotarod stability tests of vehicle-treated 8 week old mutant mice compared to vehicle-treated WT mice.
Figure 2B:
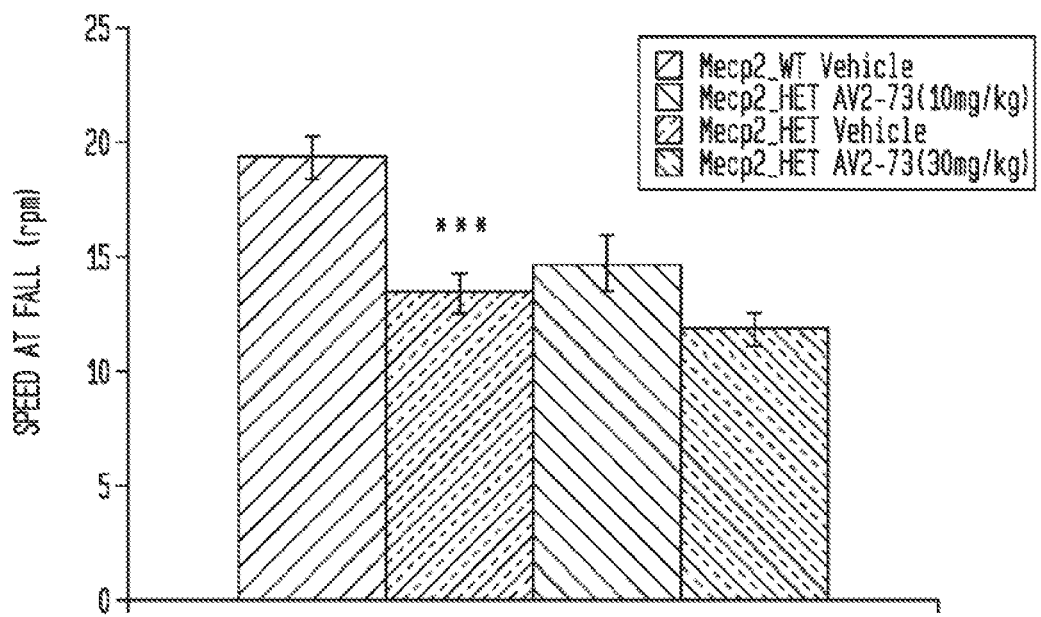

Rotarod at 8 Weeks [FIG. 2A and FIG. 2B]

Vehicle-treated mutant mice fell more rapidly and at lower speeds compared to vehicle-treated WT mice. No significant treatment effects were observed for either measure.

Figure 3A:
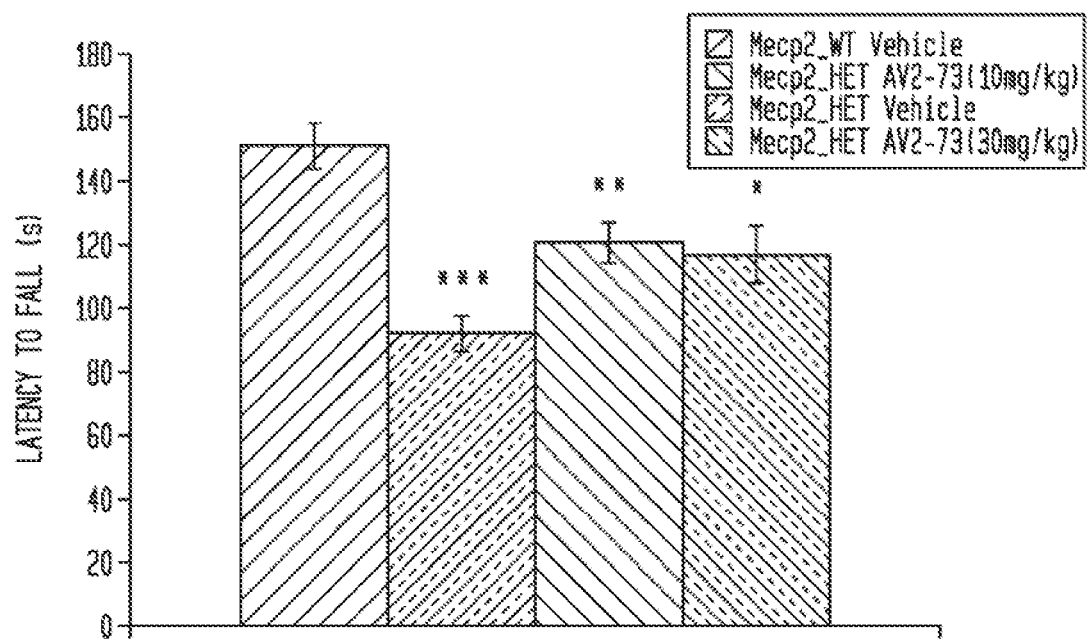
FIGS. 3A and 3B are graphic representations of rotarod stability tests of vehicle-treated 12 week old mutant mice compared to vehicle-treated WT mice.
Figure 3B:
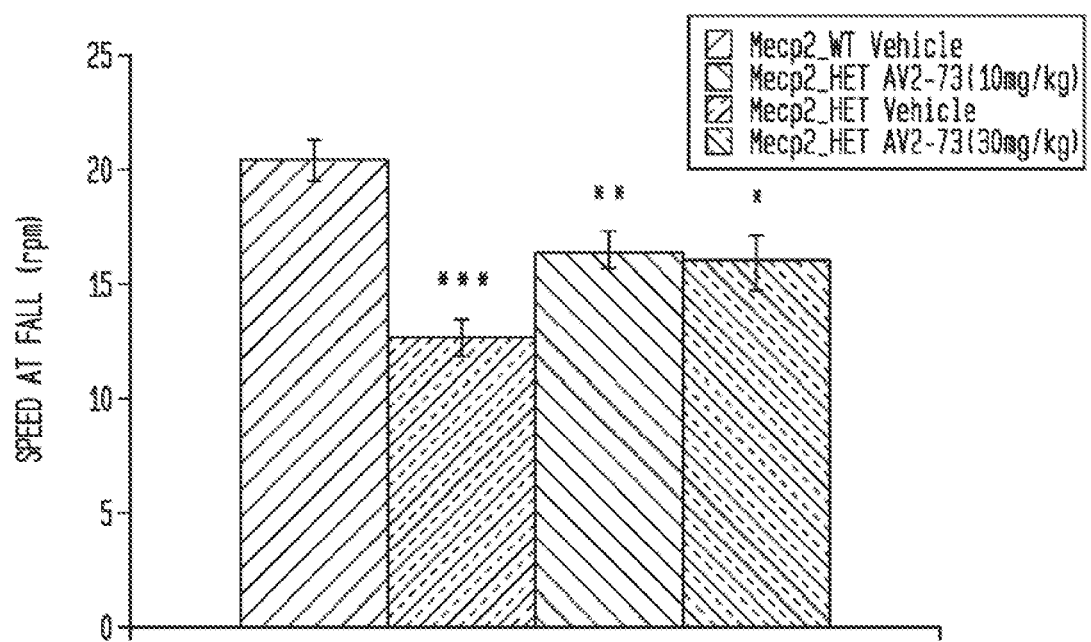

Rotarod at 12 Weeks [FIG. 3A and FIG. 3B]

Vehicle-treated mutant mice fell more rapidly and at lower speeds compared to vehicle-treated WT mice. A2-733-treated mice at both doses took more time to fall off the rod and fell at higher speeds compared to vehicle-treated mutant mice. Without outliers, the effect at the higher dose disappeared for the speed at fall measure. Mutant mice were slower and fell more quickly at both 8 and 12 weeks of age compared to wildtype controls.

Clasping [FIG. 4A and FIG. 4B]

Mice are lifted gently by the tail with front limbs remaining on surface. Clasping of hind legs is noted (normal is a spread in the hind legs).

Figure 5:
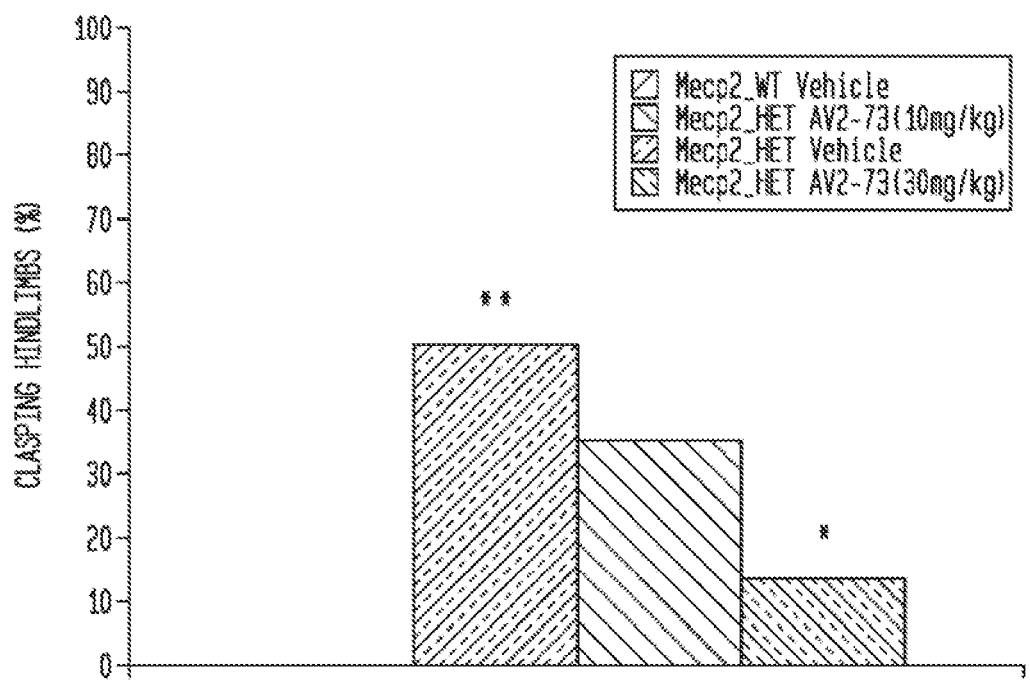
FIG. 5 is a graphic presentation of clasping responses in mutant and wildtype mice treated with A2-73.

Clasping at 8 Weeks [FIG. 5]

Vehicle-treated mutant mice clasped more than vehicle-treated wild type mice. Mice treated with A2-733 (30 mg/kg) clasped less than vehicle-treated mutant mice.

Startle/PPI

The acoustic startle measures an unconditioned reflex response to external auditory stimulation. Mice are placed in the prepulse inhibition (PPI) chambers for a 5 min session of white noise (70 dB) habituation. Then the session starts with a habituation block of 6 presentations of the startle stimulus alone, followed by 10 PPI blocks of 6 different types of trials [null (no stimuli), startle (120 dB), startle plus prepulse (4, 8 and 12 dB over background noise i.e. 74, 78 or 82 dB) and prepulse alone (82 dB)] presented at random within each block. The amount of inhibition of the normal startle is determined and expressed as a percentage of the basic startle response (from startle alone trials), excluding the startle response of the first habituation block.

Figure 6A:
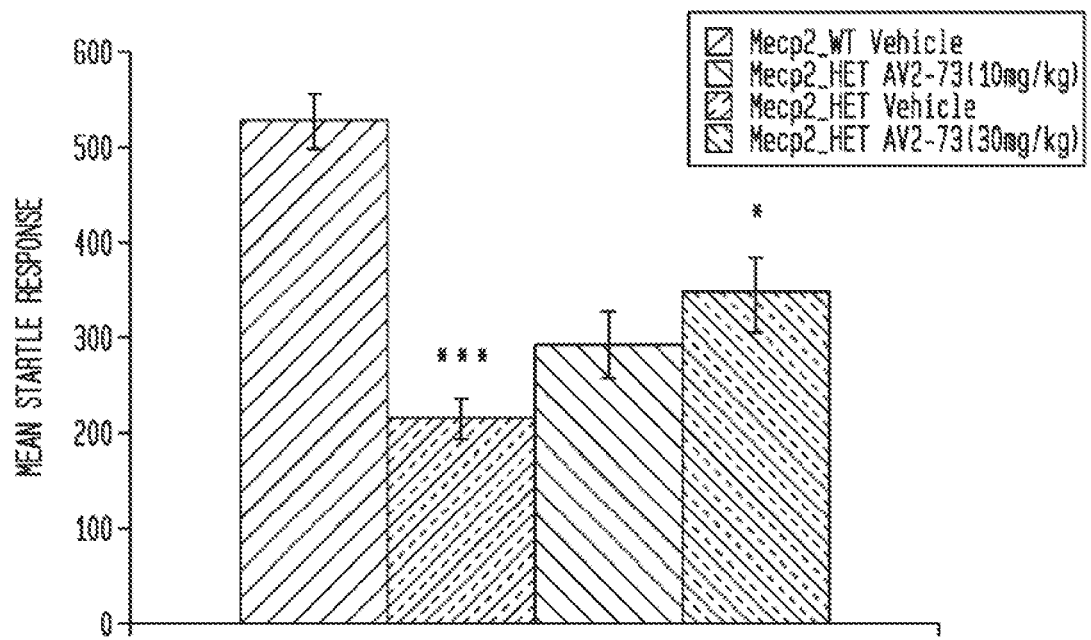
FIGS. 6A and 6B are graphic results of pre pulse inhibition (PPI) in startle response tests in mutant and wildtype 8 week old mice treated with A2-73.
Figure 6B:
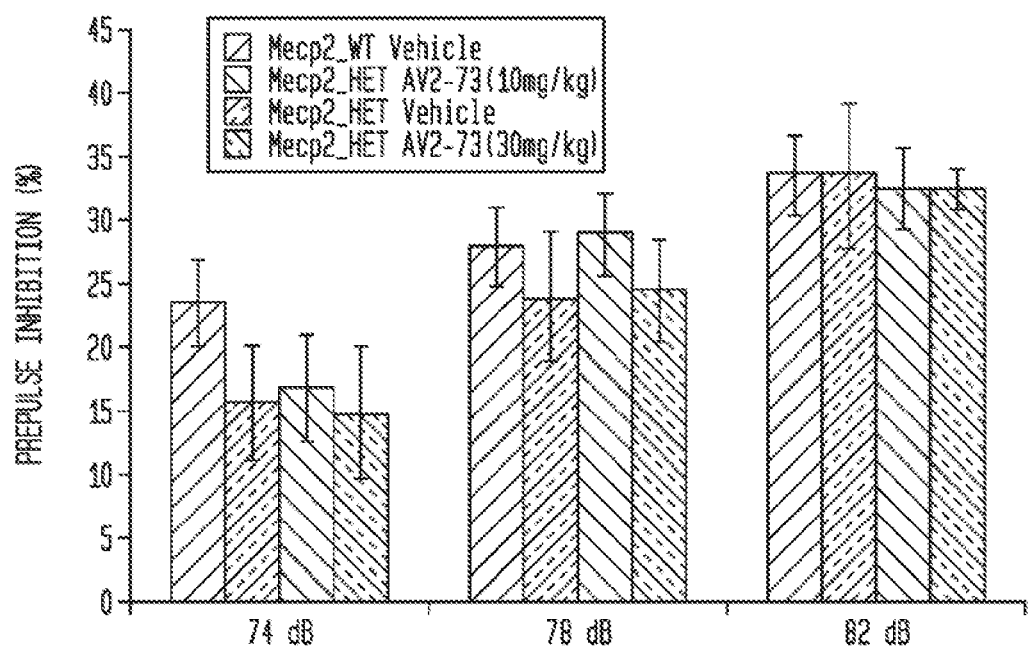

Startle/PPI 8 Weeks [FIG. 6A and FIG. 6B]

Vehicle-treated mutant mice startled less and but showed no differences in PPI response compared to vehicle-treated WT mice. A2-733 (30 mg/kg) treated mice showed an increased startle response compared to vehicle-treated mutant mice. No treatment differences were observed in PPI.

Figure 7A:
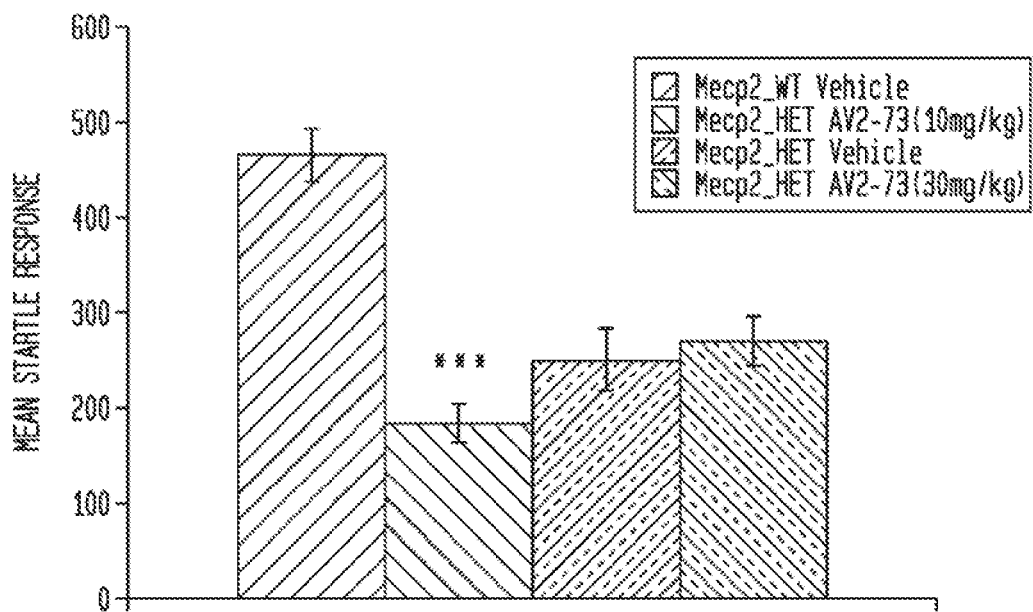
FIGS. 7A and &B are graphic results of pre pulse inhibition (PPI) in startle response tests in mutant and wildtype 12 week old mice treated with A2-73.
Figure 7B:
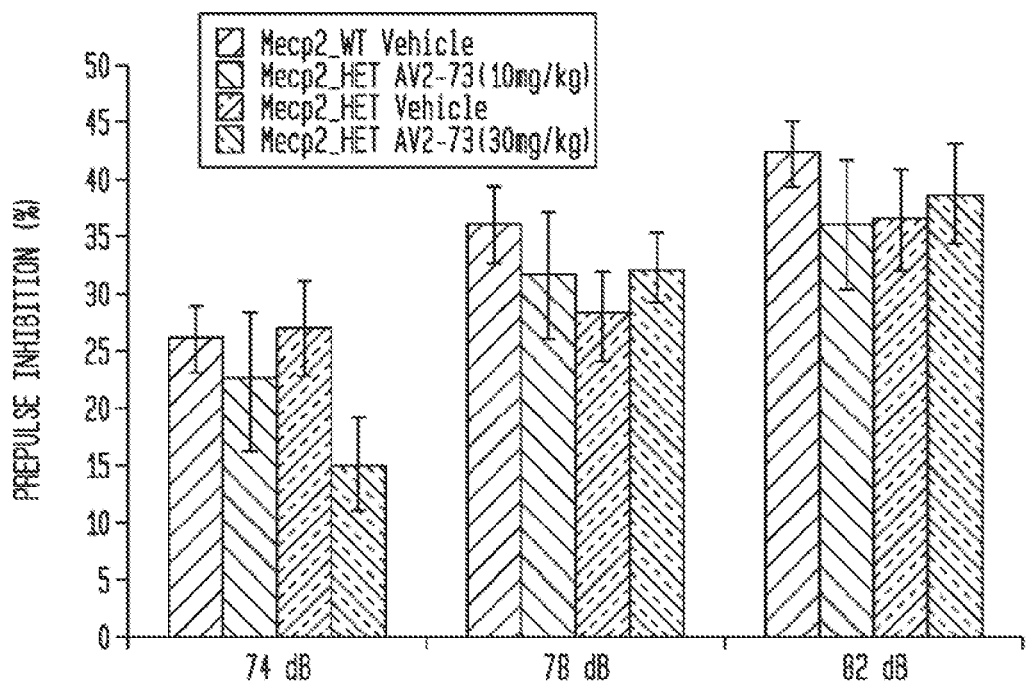
Figure 9A:
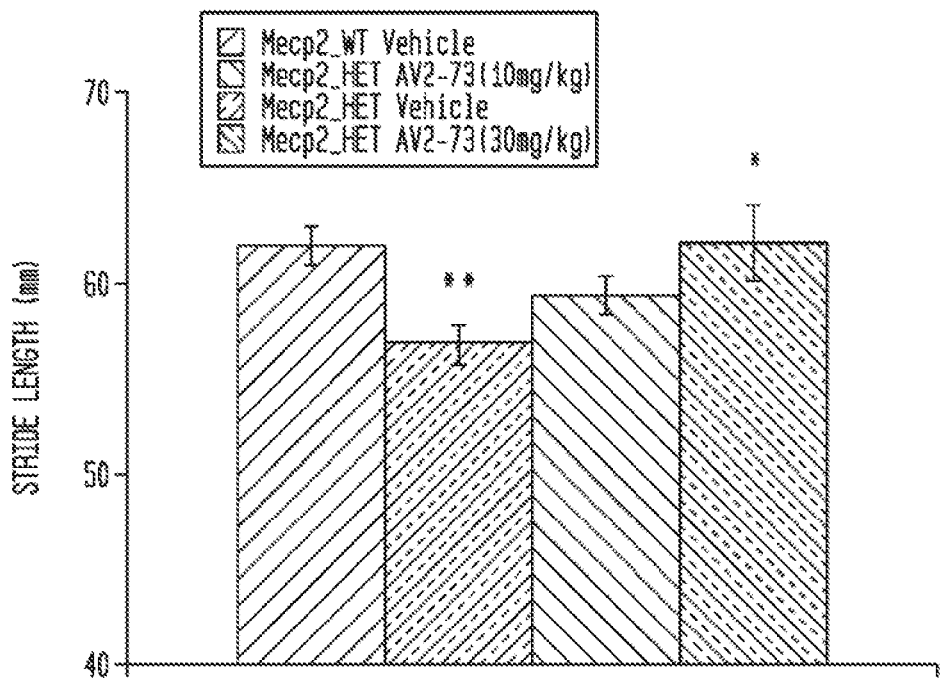
FIG. 9A-D graphically display gait differences which appeared to be rescued while others enhanced the mutant gait phenotype.
Figure 9B:
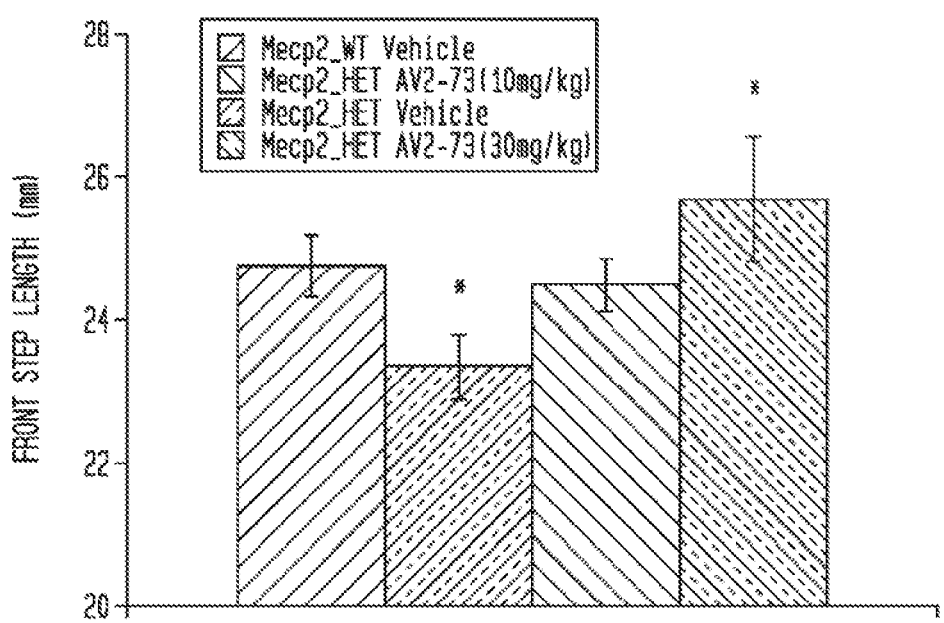
Figure 9C:
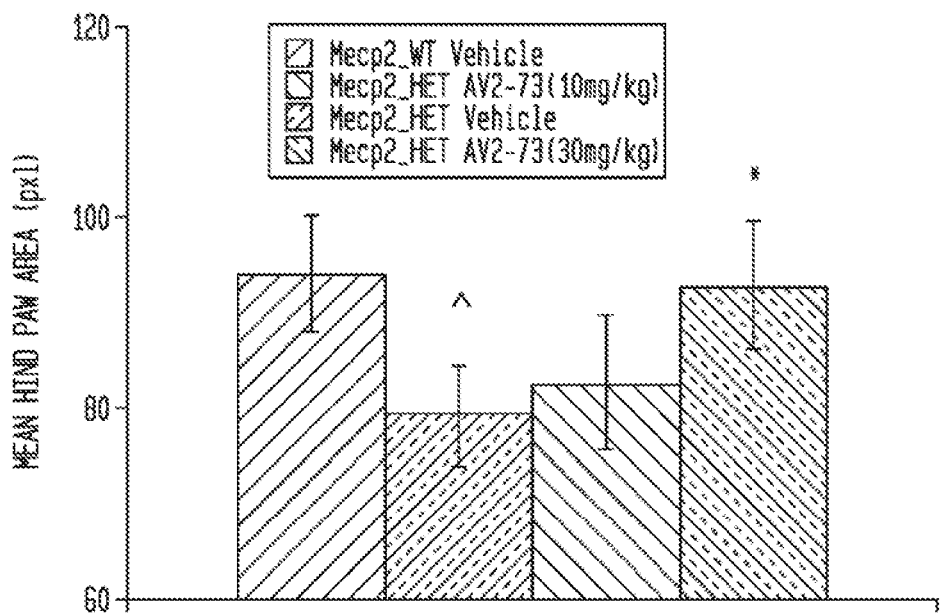
Figure 9D:
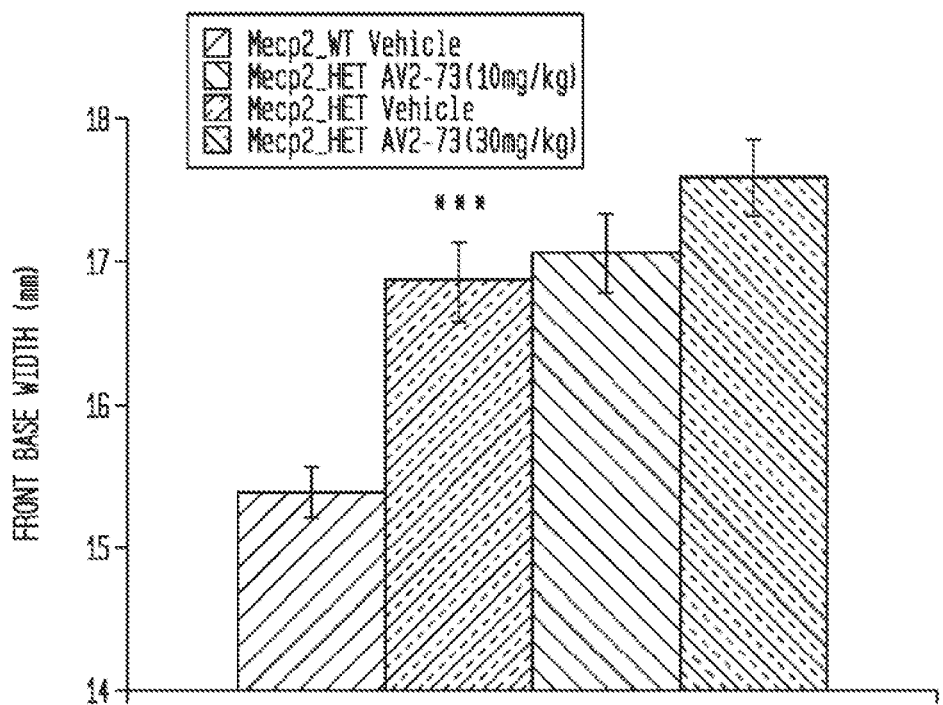

Startle/PPI 12 Weeks [FIG. 7A and FIG. 7B]

Vehicle-treated mutant mice startled less but showed no differences in PPI response compared to vehicle-treated WT mice. There was a trend of a treatment effect in the startle response ($p<0.08$). With outliers removed, this trend became significant, with A2-733 (30 mg/kg) mice showing increased startle compared to vehicle-treated mutant mice ($p<0.01$). The PPI treatment interaction ($p<0.05$) did not reveal any significant post hoc differences.

Neurological testing via a platform that employs computer vision to detect changes in gait geometry and gait dynamics in rodent models of neurological disorders, pain, and neuropathies. Complex bio-informatics algorithms similar to those used in SmartCube® are employed to detect a disease phenotype and screen compounds. (NeuroCube, PsychoGenics, Tarrytown N.Y.)

A platform that employs computer vision to detect changes in gait geometry and gait dynamics in rodent models of neurological disorders, pain, and neuropathies. Mice are allowed to walk in the chamber for 5 min. When the paw touches the screen, LED light reflects creating bright spots. Images are captured and processed using proprietary computer vision and bio-informatics data mining algorithms.

FIGS. 8A-C graphically display Neurocube 8 week data. Significant separation between WT and HET vehicle mice ($p=0$). There was no separation between A2-733 versus Het vehicle. There was 9-17% recovery of the overall signature due to mild beneficial effects of the drug on gait and imaging features.

FIGS. 9A-D graphically display gait differences which appeared to be rescued while others enhanced the mutant gait phenotype.

NeuroCube 8 week gait analysis is presented in Table 1 (below):

|  | WT vehicle v. Het vehicle | Het vehicle v. Het AV2-73, 10 mg/kg | Het vehicle v. Het AV2-73, 30 mg/kg |
| --- | --- | --- | --- |
| Overall | 90, p = 0 | 53, p > 0.69 | 62, p > 0.24 |
| GAIT | 78, p < 0.01 | 63, p > 0.09 | 69, p < 0.05 |
| Paw Features | 91, p < 0.001 | 52, p > 0.78 | 55, p > 0.56 |
| Correlation | 53, p > 0.66 | 56, p > 0.40 | 76, p < 0.005 |
| Body Motion | 71, p < 0.02 | 60, p > 0.20 | 81, p < 0.003 |
| Paw Positioning | 84, p < 0.0001 | 53, p > 0.57 | 57, p > 0.36 |

NeuroCube 12 week gait analysis is presented in Table 2 (below):

|  | WT vehicle v. Het vehicle | Het vehicle v. Het AV2-73, 10 mg/kg | Het vehicle v. Het AV2-73, 30 mg/kg |
| --- | --- | --- | --- |
| Overall | 95, p = 0 | 53, p > 0.70 | 61, p > 0.21 |
| GAIT | 77, p < 0.0001 | 57, p > 0.29 | 57, p > 0.37 |
| Paw Features | 86, p = 0 | 56, p > 0.35 | 53, p > 0.65 |
| Correlation | 76, p < 0.005 | 53, p > 0.70 | 69, p < 0.03 |
| Body Motion | 83, p = 0 | 52, p > 0.71 | 68, p < 0.04 |
| Paw Positioning | 80, p < 0.001 | 53, p > 0.57 | 53, p > 0.62 |

It is believed that therapeutic doses of A-2-73 increases lifespan and improves locomotor, respiratory, and cardiac function in children with Rett Syndrome.

EXAMPLE 1

Breathing Variability Reduction

A 6 year old female presenting with Rett syndrome is administered oral doses of A2-73 at 4 mg daily for 10 days.

On presentation, her breathing is abnormal. Her mean breaths per minute is calculated to assess breathing variability. After 10 days of A2-73, administration the 0 (breaths/minute) was significantly reduced (implying less variability).

EXAMPLE 2

Cardiac Pulse Rate

A 10 year old female presents with Rett syndrome. Her real time cardiac pulse rate is monitored. Prior to commencing therapy, her heart rate is 49 beats per minute with substantial variability. Following treatment with oral doses of A2-73 at 20 mg daily for 5 days, the variability is reduced while the average rate is increased to 75 beats per minutes.

EXAMPLE 3

Seizure Reduction

An 18 month old female presents with Rett syndrome. She experiences 6 to 10 seizures per day prior to commencing therapy. She begins treatment with oral doses of A2-73 at 2 mg daily. After 5 days of treatment, the number of daily seizures is reduced to 3 or fewer.

EXAMPLE 4

Eating and Choking

A 20 year-old female presents with Rett syndrome. She experiences feeding difficulties exhibiting as choking and poor food intake prior to commencing therapy. She begins treatment with oral doses of A2-73 at 40 mg every other day. After 60 days of treatment, the instances of choking are reduced and she exhibits a 10% weight gain.

EXAMPLE 5

Angelman—Sleep and Seizures

A 25 year-old male presents with Angelman syndrome. He experiences disturbed sleep and frequent seizures prior to commencing therapy. He begins treatment with oral doses of A2-73 at 30 mg/day. After 15 days of treatment, his sleep is markedly less disturbed and his instances of seizure are reduced by 50%.

EXAMPLE 6

Williams Syndrome—Weight Gain

A 2 year-old male presents with Williams syndrome. He exhibits a failure to thrive with low weight gain. He begins treatment with i.v. doses of A2-73 at 5 mg every other day. After 60 days of treatment, he exhibits a 10% weight gain.

EXAMPLE 7

Smith-Magenis Syndrome—Sleep

A 5 year-old male presents with Smith-Magenis syndrome. He experiences disturbed sleep. He begins treatment with oral doses of A2-73 at 10 mg/day. After 15 days of treatment, his sleep is markedly less disturbed.

EXAMPLE 8

Multiple Sclerosis

A 17 year-old male presents with multiple sclerosis. He begins treatment with oral doses of A2-73 at 40 mg every fifth day. The total number of gadolinium-enhanced lesions on MRI at weeks 12, 16, 20 and 24 is substantially reduced as compared to his 12 week pretreatment MRI.

EXAMPLE 9

Multiple Sclerosis

A 27 year-old female presents with relapsing-remitting multiple sclerosis. She begins treatment with oral doses of A2-73 at 30 mg every other day for 3 months. She exhibits a significantly lower number of total gadolinium-enhancing lesions on monthly brain MRI up to month 6.

The pharmaceutical compositions provided herein can be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also, in some embodiments, be administered by a transdermal device. Accordingly, transdermal administration can be accomplished using a patch either of the reservoir or porous membrane type, or of a solid matrix variety.

The noted components for orally administrable, injectable or topically administrable compositions are merely representative. Other materials as well as processing techniques and the like are set forth in Remington: The Science and Practice of Pharmacy, $22^{nd}$ Edition (2012), Pharmaceutical Press, which is incorporated herein by reference.

The compounds of this invention can also be administered in sustained release forms or from sustained release drug delivery systems. A description of representative sustained release materials can be found in Remington's Pharmaceutical Sciences.

What is claimed is:

1. A method of ameliorating biochemical and functional abnormalities associated with methyl-CpG binding protein 2 defects (MeCP2 defects) in a subject by administering to the subject in need thereof a composition comprising a therapeutically effective amount of a therapeutic agent selected from the group of Anavex2-73, an analog of Anavex2-73, and a combination thereof.

2. The method of claim 1, wherein the biochemical and functional abnormalities associated with MeCP2 defects manifest as neurodevelopmental or neurological diseases.

3. The method of claim 2, wherein the neurodevelopmental or neurological diseases comprises multiple sclerosis, Rett Syndrome, cerebral palsy, Angelman syndrome, Williams syndrome, pervasive developmental disorder not otherwise specified (PDD-NOS), childhood disintegrative disorder, Smith-Magenis syndrome, non-syndromic mental retardation, idiopathic neonatal encephalopathy, idiopathic cerebral palsy, or autism spectrum disorder.

4. The method of claim 1, wherein the biochemical and functional abnormalities associated with MeCP2 defects comprises abnormal breathing, abnormal cardiac function, abnormal feeding or choking, weight gain failure, abnormal sleep or seizure.

5. The method of claim 1, wherein the therapeutic agent is Anavex2-73.

6. The method of claim 1, wherein the therapeutic agent is the analog of Anavex2-73 selected from the group consisting of A1-41, A19-144, and a combination thereof.

7. The method of claim 1, wherein the therapeutically effective amount is a dosage from about 0.5 mg/day to about 100 mg/day.

8. The method of claim 1, wherein the composition is selected from a group consisting of an oral composition, a transdermal composition and a parenteral composition.

9. The method of claim 1, wherein the subject is an adult, a child, or an infant.

10. The method of claim 1, wherein the subject is a child or an infant and the dosage ranges from about 0.5 mg/day to about 20 mg/day.

11. A method of treating disorders associated with methyl-CpG binding protein 2 defects (MeCP2 defects) in a subject by administering to the subject in need thereof a composition comprising a therapeutically effective amount of a therapeutic agent selected from the group of Anavex2-73, an analog of Anavex2-73, and a combination thereof.

12. The method of claim 11, wherein the disorders associated with MeCP2 defects comprises a neurodevelopmental or a neurological disease.

13. The method of claim 12, wherein the neurodevelopmental or neurological disease comprises multiple sclerosis, Rett Syndrome, cerebral palsy, Angelman syndrome, Williams syndrome, pervasive developmental disorder not otherwise specified (PDD-NOS), childhood disintegrative disorder, Smith-Magenis syndrome, non-syndromic mental retardation, idiopathic neonatal encephalopathy, idiopathic cerebral palsy, or autism spectrum disorder.

14. The method of claim 13, wherein the neurodevelopmental or neurological diseases is treated by normalizing breathing, normalizing cardiac function, normalizing feeding and avoiding choking, obtaining weight gain, normalizing sleep or reducing seizure.

15. The method of claim 11, wherein the therapeutic agent is Anavex2-73.

16. The method of claim 11, wherein the therapeutic agent is the analog of Anavex2-73 selected from the group consisting of A1-41, A19-144, and a combination thereof.

17. The method of claim 11, wherein the therapeutically effective amount is a dosage from about 0.5 mg/day to about 100 mg/day.

18. The method of claim 11, wherein the composition is selected from a group consisting of an oral composition, a transdermal composition and a parenteral composition.

19. The method of claim 11, wherein the subject is an adult, a child, or an infant.

20. The method of claim 11, wherein the subject is a child or an infant and the dosage ranges from about 0.5 mg/day to about 20 mg/day.

* * * * *